US005472687A

United States Patent [19]

Proctor

[11] Patent Number: 5,472,687
[45] Date of Patent: Dec. 5, 1995

[54] TOPICAL PYRIDINE N-OXIDES

[76] Inventor: Peter H. Proctor, Twelve Oaks Medical Towers 4126 SW. Freeway, Suite 1616, Houston, Tex. 77027

[21] Appl. No.: 193,228

[22] Filed: Feb. 7, 1994

Related U.S. Application Data

[63] Continuation-in-part of Ser. No. 21,970, Feb. 24, 1993, Pat. No. 5,352,442, which is a continuation-in-part of Ser. No. 149,720, Jan. 29, 1988, abandoned, which is a continuation-in-part of Ser. No. 8,186, Jan. 28, 1987, abandoned, which is a continuation-in-part of Ser. No. 858,050, Apr. 30, 1986, abandoned, which is a continuation-in-part of Ser. No. 757,131, Jul. 18, 1985, abandoned.

[51] Int. Cl.$^6$ .............................. A61K 7/06; A61K 31/44
[52] U.S. Cl. .................. 424/70.1; 514/356; 514/358; 546/316; 546/318; 546/326
[58] Field of Search .................. 424/70, 70.1; 514/356, 514/358; 546/316, 318, 326

[56] References Cited

U.S. PATENT DOCUMENTS

| | | | |
|---|---|---|---|
| 2,409,754 | 10/1946 | Henze | 260/309.5 |
| 2,986,573 | 5/1961 | Topliss | 167/65 |
| 3,257,390 | 6/1966 | Patchett | 260/239.55 |
| 3,461,461 | 8/1969 | Anthony et al. | 260/256.4 |
| 3,527,864 | 9/1970 | MacMillen et al. | 424/177 |
| 3,551,554 | 12/1970 | Herschler | 424/7.1 |
| 3,896,238 | 7/1975 | Smith | 424/358 |
| 4,139,619 | 2/1979 | Chidsey, III | 424/45 |
| 4,189,039 | 1/1980 | Soldati | 544/12 |
| 4,254,145 | 3/1981 | Birnbaum | 424/305 |
| 4,327,245 | 8/1982 | Shapiro | 424/241 |
| 4,344,943 | 8/1982 | Wiechert | 424/243 |
| 4,367,227 | 1/1983 | Bingham | 424/243 |
| 4,444,762 | 4/1984 | Rajadhyaksha | 424/180 |
| 4,456,600 | 6/1984 | Wiechert | 424/238 |
| 4,596,812 | 6/1986 | Chidsey, III | 424/251 |
| 4,866,067 | 9/1989 | Di Schiena | 514/275 |
| 5,256,678 | 10/1993 | Nakaguchi | 514/346 |

FOREIGN PATENT DOCUMENTS

| | | |
|---|---|---|
| 0027655 | 4/1981 | European Pat. Off. |
| 0249397 | 12/1987 | European Pat. Off. |
| 0273202 | 7/1988 | European Pat. Off. |
| 0327263 | 8/1989 | European Pat. Off. |
| 0415598 | 3/1991 | European Pat. Off. |
| 55-22644 | 2/1980 | Japan . |
| 2198132 | 6/1988 | United Kingdom . |
| 8302558 | 8/1983 | WIPO . |
| 8600616 | 1/1986 | WIPO . |
| 8700427 | 1/1987 | WIPO . |

OTHER PUBLICATIONS

Bourayne et al., Journal de chimie physique, vol. 79, No. 2, pp. 139–147 (1982).
Anderson, Chemical Abstracts, vol. 90, pp. 311K (1979).
Ando et al., Chemical Abstracts, 93:79872n (1980).
Bazzano et al., Journal of American Academy of Dermatology, vol. 15, pp. 880–883 (1986).
Berry, Pharmacology of the Skin, vol. 1, pp. 121–137 (1987).
Cheng et al., Archives of Dermatological Research, vol. 278, pp. 470–473 (1986).
Cumming et al., Journal of American Medical Association, vol. 247, pp. 1295–1298 (1982).
Current Therapy, pp. 599–603 (1984).
Dahl, Men's Fitness, pp. 93–95 (Feb. 1989).
Dawber, Dermatologica, vol. 175, suppl. 2, pp. 23–28 (1987).
DeVillez, Archives of Dermatology, vol. 121, pp. 197–202, 1985.
Dermatologica, vol. 175, suppl. 2, pp. 1–56 (Oct. 87).
Dostert et al., Xenobiotica, vol. 15, No. 10, pp. 799–803 (1985).
Ehman et al., Investigative Radiology, vol. 21, pp. 125–131 (1986).
Feelisch et al., Evr. Journal of Pharmacology, vol. 139, pp. 19–30 (1987).
Feelisch et al., Evr. Journal of Pharmacology, vol. 142, pp. 405–409 (1987).
Fiedler, Dermatologica, vol. 175, suppl. 2, pp. 29–35 (1987).
Fox et al., Annals of the New York Academy of Sciences, vol. 411, pp. 14–19 (1983).
Goffman et al., International Journal of Radiation, Oncology, Biology and Physics, vol. 22, pp. 803–806 (Nov. 4, 1992).
Headington, Current Therapeutic Research, vol. 36, pp. 1098–1105 (1984).
Hearse et al., Circulation Research, vol. 60, pp. 375–383 (1987).
Herschler, Chemical Abstracts, vol. 78, pp. 115–239 (1973).
Ignarro et al., Biochemica et. Biophysica Acta, vol. 631, pp. 221–231 (1980).
J., Soc. Cosmetology Chem., (Italy) vol. 33, pp. 95–96 (Mar./Apr. 1982).
Journal of American Medical Association, vol. 260, No. 20 (1988).
Karlsson et al., Journal of Cyclic Nucleotide and Protein Res., vol. 10, No. 4, pp. 309–315 (1985).
Kvedar, Journal of American Academic Dermatology, vol. 12, pp. 215–225 (1985).
Longevity, vol. 2, No. 3, p. 26 (Jan. 1988).
Lucky, Archives of Dermatology, vol. 121, pp. 57–62 (1985).
Messina, Current Therapeutic Research, vol. 34, pp. 319–324 (1983).
Messina, Current Therapeutic Research, vol. 38, pp. 269–282 (1985).
Mitchell et al., IBC USA Conference, South Natick, Mass. (Jun. 27, 1991).
Mittal et al., Proc. of National Academy of Science, USA, vol. 74, No. 10, pp. 4360–4364 (1977).

(List continued on next page.)

Primary Examiner—Porfirio Nazario-Gonzales
Attorney, Agent, or Firm—Sroufe, Payne & Lundeen

[57] ABSTRACT

Topical pyridine N-oxides, including 3-carboxypyridine N-oxide, niacinamide N-oxide, and α-(4-pyridyl-1-oxide)-N-t-butylnitrone, are disclosed. The topical compositions have utility in a topical pharmaceutical formulation for the cosmetic treatment of hair loss and the cosmetic stimulation of hair growth.

10 Claims, No Drawings

OTHER PUBLICATIONS

Palmer et al., *Nature*, vol. 327, pp. 524–526 (Jun. 11, 1987).

Parrett et al., *Journal of Pharmacology*, vol. 91, pp. 49–59 (1987).

*Physician's Desk Reference*, pp. 883, 977–978, 1782–1785, 1961 (1983).

Proctor et al., *Physiological Chemistry and Physics in Medical NMR*, vol. 16, pp. 175–195 (1984).

Ross, U.S. Department of Commerce, National Bureau of Standards, *Publication NSRDS-NBS59* (Jan. 1977).

Sekura, *Advances of Biology and Skin*, vol. XII, pp. 257–269, (1972).

Shapiro et al., *Journal of Clinical Endocrinology and Metabolism*, vol. 51, pp. 429–430 (1980).

Stewart, *International Journal of Dermatology*, vol. 17, pp. 167–179 (1978).

Thompson, *Federal Drug Administration Consumer*, pp. 10 and 12 (Mar. 10, 1981).

Tiffany–Castiglion, *Biochemical Pharmacology*, vol. 31, No. 2, pp. 181–188 (1982).

Torre (Ed.), *Annals of the New York Academy of Sciences*, vol. 411, Table of Contents (1983).

Vermorken, *Acta Dermatovener* (Stockholm), vol. 63, pp. 268–269 (1982).

Voorhees (Ed.), *Dermatologica*, vol. 175, suppl. 2, pp. 1–56 (1987).

Watanabe et al., *Archives of Dermatological Research*, vol. 278, pp. 470–473 (1986).

Weissmann, *Archives of Dermatology*, vol. 121, pp. 57–62 (1985).

Yoshioka et al., *Archives of Dermatological Research*, vol. 278, pp. 177–183 (1986).

Proctor, *Archives of Dermatology*, p. 1146 (Aug. 1989).

TOPICAL PYRIDINE N-OXIDES

CROSS-REFERENCE TO RELATED APPLICATIONS

This application is a continuation-in-part of application Ser. No. 08/021,970, filed Feb. 24, 1993; now U.S. Pat. No. 5,352,442 which is a continuation-in-part of application Ser. No. 07/149,720, filed Jan. 29, 1988, abandoned; which is a continuation-in-part of application Ser. No. 07/008,186, Jan. 28, 1987, abandoned; which is a continuation-in-part of application Ser. No. 06/858,050, Apr. 30, 1986, abandoned; which is a continuation-in-part of application Ser. No. 06/757,131, Jul. 18, 1985, abandoned.

FIELD OF THE INVENTION

This invention relates to topical pyridine N-oxide, and the treatment of hair loss therewith.

BACKGROUND OF THE INVENTION

Recently, several anti-alopecia agents such as minoxidil and cyoctol have gained attention. However, most of these anti-alopecia agents are only minimally effective in some cases and/or can cause adverse dermatological or systemic reactions. Minoxidil, for example, is a therapeutic antihypertensive. Thus, the search continues for new, safer and more effective anti-alopecia agents which can be used without the risk of undesirable antihypertensive and other side effects.

SUMMARY OF THE INVENTION

Applicant has discovered that pyridine N-oxide can be used as a topical anti-alopecia agent, which can desirably be essentially free of antihypertensives, for example, to stimulate cosmetic hair growth.

DETAILED DESCRIPTION OF THE INVENTION

In the present invention, pyridine N-oxide is compounded in a topical formulation. The pharmaceutical carrier, in which the pyridine N-oxide is generally substantially homogeneously dispersed can be an aqueous dispersion or suspension, or a water-in-oil or oil-in-water emulsion. Pharmaceutical carriers which can be mentioned include water, urea, alcohols and glycols such as methanol, ethanol, propanol, butanol, ethylene glycol, propylene glycol, and the like.

Suitable water-in-oil emulsions are commercially available under the designations Aquaphor, cold cream, Eucerin, hydrous lanolin, Hydrosorb hydrophilic petrolatum, Nivea, Polysorb, Qualatum and Velvachol. Suitable oil-in-water emulsions are available commercially under the designations acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi. The carrier may further contain various other emollients, emulsifiers, water, perfumes, colorants, preservatives, and the like. The topical formulation is in the form of a cream, lotion, shampoo, cream rinse, or the like.

Pyridine N-oxide is commercially available. The pyridine N-oxide can be unsubstituted, but is preferably substituted in the 2, 3 or 4 position with a carboxylate, carboxamide, N-t-butylnitrone, or the like. The carboxylate-substituted pyridine N-oxide can be salified or esterified. The niacin N-oxides, e.g. 3-carboxypyridine N-oxide and niacinamide N-oxide, are preferred. There can also be mentioned 4-substituted-2,2,6,6-tetralkyl-3H,5H-pyridine N-oxide.

Effective amounts of the pyridine N-oxide generally range from about 0.01 to about 20% by weight of the topical composition, more preferably from about 0.1 to about 10% by weight, most preferably from about 0.5 to about 3% by weight, but more or less can be present in the composition depending on the particular pyridine N-oxide formulation and the treatment conditions.

The topical pyridine N-oxide can be used alone or in combination with other hair growth stimulants or additaments which are available to enhance the function of the hair growth stimulant, such as, for example, the hydroxyl radical scavengers, antiandrogens and others described in International Publication No. WO 87/00427 (International Application No. PCT/US86/01393) published on Jan. 29, 1987; and European Patent Application No. 89300785.6, Publication No. 0327263/A1, published Aug. 9, 1989; both of which are hereby incorporated in their entirety herein as though fully set forth verbatim, including reference therein to the publication of Ross & Ross, "Selected Specific Rates of Reactions of Transients From Water In Aqueous Solution. III. Hydroxyl Radical and Pure Hydroxyl Radicals and Their Radical Ions," National Standard Reference Data Series, National Bureau of Standards, 59 (1977), which is also incorporated herein by reference.

According to the present invention, the topical pyridine N-oxide is applied to the skin to be treated, such as the scalp. Depending on the type of hair loss or alopecia being treated and the conditions thereof, the stimulation of hair growth can usually be obtained by topical application, preferably repeated daily application for a period of 3–6 months. The utility of topical pyridine N-oxide is not limited thereto, however, and the stimulation of hair growth can include an increased rate of growth, increased hair diameter, follicular neogenesis, and the like, as well as inhibiting hair loss or alopecia from progressing, for example, in male pattern baldness, or during the course of treatment with other therapeutic agents known to induce hair loss, such as chemotherapy or radiation therapy in cancer treatment. The topical pyridine N-oxide can, if desired, be essentially free of minoxidil and other antihypertensives for use by individuals sensitive to them.

The invention is illustrated by way of the following examples:

EXAMPLE 1

A medicated shampoo was prepared by adding 500 mg of nicotinic acid N-oxide (NANO) to a commercially available non-medicated shampoo, and allowing the mixture to dissolve for 2–3 days. The shampoo was then used in a normal manner 2–7 times per week, e.g. wetting the hair, working a small amount (5–20 ml) of the shampoo into the hair and scalp, and rinsing after 1–3 minutes of contact with the scalp. Stimulation of hair growth was observed in 2–4 months.

EXAMPLE 2

NANO was suspended in deionized water at 1 g/100 ml. The suspension was applied twice daily to thinning areas of the scalp at 8–10 drops per application. Stimulation of hair growth was observed in 2–4 months.

EXAMPLE 3

A formulation was prepared by mixing the following together:

| Ingredient | Amount |
| --- | --- |
| Water | 1600 ml |
| Spironolactone | 100 g |
| NANO | 50 g |
| BHT | 50 g |
| Ascorbyl Palmitate | 50 g |
| Minoxidil | 1.2 g |
| Phenytoin | 50 g |
| Tretinoin | 2 g |
| Arginine | 50 g |

The mixture was then blended together with 900 ml of dimethylsulfoxide and 4.08 kg of Dermavan cream vehicle to make a lotion. Daily topical application gives better hair growth stimulation than compared to any component alone.

The invention is described above and illustrated herein with reference to specific chemical formulas, preparations and therapeutic and cosmetic applications. Many variations and modifications will become apparent to those skilled in the art in view of the foregoing disclosure. It is intended that the following claims are not to be limited thereby, and are to be construed in accordance with the spirit and scope thereof.

I claim:

1. Substituted or unsubstituted pyridine N-oxide in a topical pharmaceutical carrier comprising an oil and water emulsion suitable for treating hair loss.

2. The composition of claim 1 comprising $\alpha$-(4-pyridyl-1-oxide)-N-t-butylnitrone.

3. The composition of claim 1, essentially free of antihypertensives.

4. The composition of claim 3 comprising a carboxylate substituent in the 2, 3 or 4 position of the pyridine N-oxide.

5. The composition of claim 4 comprising 3-carboxypyridine N-oxide.

6. The composition of claim 5 wherein the carboxypyridine is salified or esterified.

7. The composition of claim 1 comprising a carboxamide substituent in the 2, 3 or 4 position of the pyridine N-oxide.

8. The composition of claim 7 comprising niacinamide N-oxide.

9. Substituted or unsubstituted pyridine N-oxide in a topical pharmaceutical carrier comprising a shampoo suitable for treating hair loss.

10. Substituted or unsubstituted pyridine N-oxide in a topical pharmaceutical carrier comprising ethylene glycol or propylene glycol suitable for treating hair loss.

* * * * *